(12) United States Patent
Wataya et al.

(10) Patent No.: US 7,407,984 B2
(45) Date of Patent: Aug. 5, 2008

(54) TETRAOXASPRIRO ANTI-MALARIALS

(75) Inventors: Yusuke Wataya, Okayama (JP); Hye-Sook Kim, Okayama (JP); Masatomo Nojima, Osaka (JP)

(73) Assignee: Okayama University, Okayama (JP)

(*) Notice: Subject to any disclaimer, the term of this patent is extended or adjusted under 35 U.S.C. 154(b) by 308 days.

(21) Appl. No.: 10/507,640

(22) PCT Filed: Mar. 11, 2003

(86) PCT No.: PCT/JP03/02864

§ 371 (c)(1),
(2), (4) Date: Feb. 15, 2005

(87) PCT Pub. No.: WO03/076425

PCT Pub. Date: Sep. 18, 2003

(65) Prior Publication Data

US 2005/0131058 A1 Jun. 16, 2005

(30) Foreign Application Priority Data

Mar. 11, 2002 (JP) ............................ 2002-065870

(51) Int. Cl.
*A61K 31/357* (2006.01)
(52) U.S. Cl. .................. 514/450; 549/336; 549/333
(58) Field of Classification Search ............... 514/450; 549/336, 333
See application file for complete search history.

(56) References Cited

FOREIGN PATENT DOCUMENTS

JP 2000-229965 A 8/2000
WO WO 93/07119 A1 4/1993

OTHER PUBLICATIONS

Yuji Nonami, Takahiro Tokuyasu, Araki Masuyama, Masatomo Nojima, Kevin J. McCullough, Hye-Sook Kim and Yusuke Wataya "Synthesis, crystal structure and anti-malarial activity of functionalized spiro-1,2,4,5-tetraoxacycloalkanes from unsaturated hydroperoxy peracetals" Tetrahedron Letters 2000, 41, 4681-4684.*
Kim et. al. "Synthesis and Antimalarial Activity of Novel Medium-Sized 1,2,4,5-Tetraoxacycloalkanes" Journal of Medicinal Chemistry 2001, 44, 2357-2361.*
Yuji Nonami et al., "Synthesis, Crystal Structure and Antimalarial Activity of Functionalized Spiro-1,2,4,5-Tetraoxacycloalkanes From Unsaturated Hydroperoxy Peracetals", Tetrahedron Letters, (2000), vol. 41, No. 23, pp. 4681-4684.
Translated under the supervision of Hiroshi Nagase, "Saishin Soyaku Kagaku", last volume, Technomics, Inc., 1993, pp. 368-372.
Kaoru Tsuchiya et al., "Synthesis, Crystal Structure and Anti-Malarial Activity of Novel Spiro-1,2,4,5-Tetraoxacycloalkanes", Tetrahedron Letters, (1999), vol. 40, No. 21, pp. 4077-4080.
Hye-Sook Kim et al., "Synthesis and Antimalarial Activity of Novel Medium-Sized 1,2,4,5-Tetraoxacycloalkanes", J. Med. Chem., 2001, vol. 44, No. 14, pp. 2357-2361.
Yuji Nonami et al., "Synthesis of Novel Hydroperoxy-Substituted 1,2,4,5-Tetroxepanes and 1,2,4,5-Tetroxocanes", 1998, vol. 39, No. 36, pp. 6597-6600.

* cited by examiner

Primary Examiner—Rita Desai
Assistant Examiner—David K O'Dell
(74) Attorney, Agent, or Firm—Venable LLP; Ann S. Hobbs; Robert Kinberg

(57) ABSTRACT

The present invention is to provide an antimalarial agent having excellent antimalarial activity with little side effects, in particular, having remarkable antimalarial activity against drug-resistant malaria parasites, and being capable of increasing solubility not only to organic solvent including olive oil, but also to water, and therefore, being usable not only as oral drugs but also as injectable solutions. The antimalarial agent of the present invention contains a compound represented by the following general formula (I) [wherein Z represents an unsubstituted or optionally substituted alicyclic hydrocarbon group, $R^0$ represents a water-soluble functional group, m represents any one of integers of from 0 to 6, n represents any one of integers of from 0 to 10.].

2 Claims, No Drawings

TETRAOXASPIRO ANTI-MALARIALS

CROSS-REFERENCE TO RELATED APPLICATION

This application is a 371 of PCT/JP03/02864, filed Mar. 11, 2003, and claims the priority of Japanese application no. 2002-065870, filed Mar. 11, 2002, the subject matter of which is incorporated herein by reference.

1. Technical Field

The present invention relates to a novel compound and an antimalarial agent being useful for the prevention and treatment of an infection caused by malaria parasites.

2. Background Art

Malaria is an infectious disease caused by an infection with a parasite which belongs to *Plasmodium*, transmitted by *Anopheles* spp., and shows symptoms such as intermittent paroxysm of fever, anemia, splenomegaly, etc. Malaria is a globally significant disease that has begun to spread rampantly along with the changes in nature and environment recently, and the number of malaria patients is estimated at 300 to 500 million, and 1.5 to 3 million people die from malaria every year. The examples of malaria parasites that infect human include: *P. falciparum* being distributed in whole tropical areas in Africa, Asia and Latin America; *P. vivax* being distributed in part of tropical and temperate zones around the world; *P. malariae* being distributed around the world; and *P. ovale* being distributed mainly in tropical western Africa. Among them, *P. falciparum* causes the most severe symptoms: it progresses to severe malaria easily at 1 or 2 weeks after the onset of disease, accompanied with encephalopathy, nephropathy, hemolytic anemia, pulmonary edema, heart damage, severe enterocolitis, etc., and in many cases, host patients show multiple organ failure in a short period of time, and it leads to the death of the patients.

Recently, there emerge insecticide-resistant mosquitoes and malaria parasites being resistant to chloroquine, that has been frequently used as an effective drug for malaria, and it is becoming difficult to deal with these organisms. In addition, the areas in danger of malaria infection are expanding along with global warming, that is, it has been detected that malaria is spread to part of temperate areas. Therefore, in today's world wherein global communication has become an every day affair, to find a cure for malaria is becoming a more and more important issue for not only WHO as a specialized agency but also all human beings. Examples of known antimalarial agent or antimalarial compound include: a novel compound of ortho-condensation system containing two heterocycles as described in Japanese Laid-Open Patent Application No. 2000-7673; an antimalarial agent containing a compound having ICAM-1 expression suppressing activity as an active component as described in Japanese Laid-Open Patent Application No. 11-228446; an antimalarial agent containing a nucleoside derivative and the like such as 5'-o-sulfamoyl-2-chloroadenosine or the like as an active component as described in Japanese Laid-Open Patent Application No. 11-228422; an antimalarial agent containing tricothecenes and the like as an active component as described in Japanese Laid-Open Patent Application No. 11-228408; an antimalarial agent containing cycloprodigiosin and the like as an active component as described in Japanese Laid-Open Patent Application No. 10-265382; a drug for preventing or treating malaria containing riminophenazine as an active component as described in Japanese Laid-Open Patent Application No. 8-231401; an agent for overcoming antimalarial drug resistance containing a quinoline derivative and the like as an active component as described in Japanese Laid-Open Patent Application No. 8-73355; an antimalarial agent containing 5-fluoroorotic acid and sulfamonomethoxyne as an active component as described in Japanese Laid-Open Patent Application No. 8-59471.

On the other hand, for malaria parasites being resistant to chloroquine, a representative drug currently used, chloroquine analogues including primaquine and mefloquine, and peroxy cyclic compound including artemisinin are useful, in particular, artemisinin, which is isolated from plants that belong to Asteraceae and has a trioxa structure, has been used as a therapeutic drug. However, a malaria parasite which shows resistance also to artemisinin, etc., has already emerged. Malaria parasites being resistant to novel malarial agents are emerging one after another, and expansion of drug-resistant malaria parasites becomes a problem for chemical therapy. Although there is quinine as an only drug being effective to drug-resistant malaria, it is very likely that renal failure is caused by quinine, and therefore, quinine is a high-risk therapeutic drug from the standpoint of the present medical standard. Under these conditions, the development of a novel drug having high antimalarial activity and being highly safe is desired. As compounds being analogous to the compound of the present invention, for example, organic peroxide compounds described in Japanese Patent Publication No. 59-46266 and Japanese Laid-Open Patent Application No. 8-67704 are known, however, these are used only as an initiator in manufacture of polymer.

The object of the present invention is to provide a novel compound being effective to malaria parasites which is resistant to various antimalarial agents, having little side effects, increasing solubility in organic solvent including olive oil, and in water, and therefore being applicable not only to oral drugs but also to injectable solutions, and to provide an antimalarial agent containing the compound as an active component.

DISCLOSURE OF THE INVENTION

The present inventors have already reported that a peroxide derivative is useful as an antimalarial agent being effective to malaria parasites which is resistant to various antimalarial agents, and having little side effects (Japanese Laid-Open Patent Application No. 12-229965). Though the peroxide derivative shows excellent antimalarial activity, it can be administered only orally because of its poor solubility. However, the present inventors have introduced a water-soluble functional group into the peroxide derivative to improve its poor solubility, and further, the present inventors have esterified the derivative and obtained ester, and found that the obtained ester is water-soluble and can be used as not only as an orally-administered drug but also as an injection drug. The present invention has been thus completed.

The present invention relates to a compound represented by the general formula (I);

(Chemical formula 6)

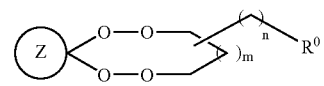

(I)

[wherein Z represents an unsubstituted or optionally substituted alicyclic hydrocarbon group, $R^0$ represents a water-soluble functional group, m represents any one of integers of from 0 to 6, n represents any one of integers of from 0 to 10.], the compound according to "1", wherein in the general formula (I), Z represents an alicyclic hydrocarbon group having from 6 to 12 carbon atoms which optionally has a lower alkyl group as a substituent ("2"), the compound according to "1" or "2", wherein in the general formula (I), Z represents any one of six-, seven-, ten-, and twelve-membered rings ("3"), the compound according to any one of "1" to "3", wherein in the general formula (I), $R^0$ represents any one of hydroxyl, carboxyl, alkoxycarbonyl, and unsubstituted or optionally substituted carbamoyl groups; n represents any one of integers of from 1 to 10 when $R^0$ represents a hydroxyl group, and any one of integers of from 0 to 9 when $R^0$ represents any one of carboxyl, alkoxycarbonyl, and unsubstituted or optionally substituted carbamoyl groups ("4"), the compound according to "4", wherein in the general formula (I), $R^0$ represents an alkoxycarbonyl group represented by the general formula (II);

(Chemical Formula 7)

—COOR¹ (II)

[wherein $R^1$ represents an unsubstituted or optionally substituted alkyl group having from 1 to 3 carbon atoms.] ("5"), the compound according to "4", wherein in the general formula (I), $R^0$ represents a carbamoyl group represented by the general formula (III);

(Chemical Formula 8)

—CONR²R³ (III)

[wherein $R^2$ and $R^3$ independently represent a hydrogen atom, or an unsubstituted or optionally substituted methyl group or ethyl group.] ("6"), the compound according to "6", wherein in the general formula (III), $R^2$ and $R^3$ independently represent an optionally substituted methyl group or ethyl group ("7"), the compound according to any one of "1" to "3", wherein in the general formula (I), $R^0$ represents the general formula (IV)

(Chemical formula 9)

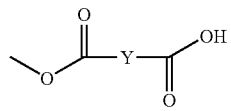

(IV)

("8"), the compound according to "8", wherein in the general formula (IV), Y represents an alkylene group ("9"), the compound according to "9", wherein the alkylene group represents any one of ethylene, tetramethylene, and hexamethylene groups ("10") and the compound according to "8", wherein in the general formula (IV), Y represents the general formula (V)

(Chemical formula 10)

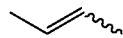

(V)

("11").

The present invention also relates to the compound according to "8", wherein in the general formula (IV), Y represents a phenylene group ("12"), a pharmaceutically acceptable salt of the compound according to "1" to "12" ("13"), and an antimalarial agent containing the compound according to "1" to "12", and/or the salt according to "13", as an active component.

BEST MODE OF CARRYING OUT THE INVENTION

The novel compound of the present invention is not particularly limited as long as it is a compound represented by the general formula (I), wherein Z represents an unsubstituted or optionally substituted alicyclic hydrocarbon group, $R^0$ represents a water-soluble functional group, m represents any one of integers of from 0 to 6, n represents any one of integers of from 0 to 10. A compound, wherein in the general formula (I), Z represents an alicyclic hydrocarbon group having from 6 to 12 carbon atoms which optionally has lower alkyl group as a substituent, is preferable, and a compound, wherein Z represents any one of six-, seven-, ten-, and twelve-membered rings, is more preferable. Further, a compound, wherein in the general formula (I), $R^0$ represents any one of hydroxyl, carboxyl, alkoxycarbonyl, and unsubstituted or optionally substituted carbamoyl groups; n represents any one of integers of from 1 to 10 when $R^0$ represents a hydroxyl group, and any one of integers of from 0 to 9 when $R^0$ represents any one of carboxyl, alkoxycarbonyl, and unsubstituted or optionally substituted carbamoyl groups, is preferable, and a compound, wherein in the general formula (I), $R^0$ represents an alkoxycarbonyl group represented by the general formula (II) wherein $R^1$ represents an unsubstituted or optionally substituted alkyl group having from 1 to 3 carbon atoms, or a compound, wherein in the general formula (I), $R^0$ represents a carbamoyl group represented by the general formula (III) wherein $R^2$ and $R^3$ independently represent any one of a hydrogen atom, an unsubstituted or optionally substituted methyl group or ethyl group, is more preferable. A compound, wherein in the general formula (III), $R^2$ and $R^3$ independently represent a methyl group or ethyl group optionally having a hydroxyl group as a substituent, is still more preferable.

In addition, the novel compound of the present invention is a compound wherein in the general formula (I), $R^0$ represents the general formula (IV), and is preferably a compound wherein in the general formula (IV), Y represents an alkylene group that represents any one of ethylene, tetramethylene, and hexamethylene groups, a compound wherein in the general formula (IV), Y represents the general formula (V), or a compound wherein in the general formula (IV), Y represents a phenylene group.

The antimalarial agent of the present invention contains the novel compound mentioned above and a pharmaceutically acceptable salt thereof as an active component.

In the general formula (I) of the present invention, Z represents an unsubstituted or optionally substituted alicyclic hydrocarbon group, and is not particularly limited as long as it is an alicyclic hydrocarbon group, however, a saturated alicyclic hydrocarbon group is preferable. Examples of alicyclic hydrocarbon group include, for instance, alicyclic hydrocarbon groups having a single ring, such as, a cyclopropylidene group, a cyclobutylidene group, a cyclopentyliden group, a cyclohexylidene group, a cycloheptylidene group, a cyclooctylidene group, a cyclononylidene group, a cyclodecylidene group, a cycloundecylidene group, a cyclododecylidene group, etc.; alicyclic hydrocarbon groups having a bridge ring or many rings, such as, a bicyclobutylidene group, a bicyclooctylidene group, a bicyclononylidene group, a norbornylidene group, an adamantylidene group, etc. With regard to these groups, the smaller the number of members in a ring in them, the more they can increase water-solubility of a compound represented by the general formula (I), and as a preferable alicyclic hydrocarbon group, an alicyclic hydrocarbon group having a single ring, or an adamantylidene group, having from 6 to 12 carbon atoms is exemplified, and more preferably, an alicyclic hydrocarbon group having 6, 7, 10 or 12 carbon atoms, specifically, a cyclohexylidene group, a cycloheptylidene group, a cyclodecylidene group, a cyclododecylidene group, an adamantylidene group, or the like, is exemplified.

The substituent being optionally possessed by the alicyclic hydrocarbon group of Z mentioned above is not particularly limited, and examples include a linear or branched alkyl group such as a methyl group, an ethyl group, an n-propyl group, an i-propyl group, an n-butyl group, an i-butyl group, a sec-butyl group, a tert-butyl group, a pentyl group having a straight chain or a side chain; and a linear or branched lower alkoxy group having from 1 to 6 carbon atoms such as a methoxy group, an ethoxy group, an n-propoxy group, an i-propoxy group, an n-butoxy group, an i-butoxy group, a sec-butoxy group, a tert-butoxy group, a pentyloxy group having a straight chain or a side chain. Preferably, a lower alkyl group having from 1 to 6 carbon atoms is exemplified, and more preferably, a tert-butyl group is exemplified.

In the general formula (I) of the present invention, an oxo ring constitutes an alicyclic hydrocarbon group represented by Z mentioned above and spiro hydrocarbon, and is not particularly limited as long as it is an alicyclic hydrocarbon group of seven- to thirteen-membered ring having a 1,2,4,5-tetraoxane ring wherein 2 peroxy groups are bound to a spiro atom.

As for a substituent which binds to the oxo ring in the general formula (I) mentioned above, there is no particular limitation as long as it is a substituent wherein a water-soluble functional group represented by $R^0$ binds to the oxo ring directly or through a carbon chain, however, as for the water-soluble functional group represented by $R^0$ in the general formula (I), a hydroxyl group, a carboxyl group, an alkoxycarbonyl group, and an unsubstituted or optionally substituted carbamoyl group, etc., are preferable. In case where these functional groups are a carboxyl group, an alkoxycarbonyl group, and an unsubstituted or optionally substituted carbamoyl group, it is preferable to bind to a terminus of an oxo ring directly or through a carbon chain, and in case the functional group is a hydroxyl group, it is preferable to bind to an oxo ring by binding to a terminus of a carbon chain. As for a carbon chain in case where these water-soluble functional groups $R^0$ bind to an oxo ring through a carbon chain, it is preferable that when $R^0$ represents a hydroxyl group in the general formula (I), n represents any one of integers of from 1 to 10, and specific examples are an alkylene group having from 1 to 10 carbon atoms in a methylene group, an ethylene group, a propylene group, an n-butylene group, an n-pentylene group, an n-hexylene group, an n-heptylene group, an n-octylene group, an n-nonylene group, an n-decylene group, and that when $R^0$ represents any one of carboxyl, alkoxycarbonyl, and unsubstituted or optionally substituted carbamoyl groups in the general formula (I), n represents any one of integers of from 0 to 9, and specific examples are an alkylene group having 9 or less carbon atoms in a methylene group, an ethylene group, a propylene group, an n-butylene group, an n-pentylene group, an n-hexylene group, an n-heptylene group, an n-octylene group, an n-nonylene group. A compound represented by the general formula (I) and having a substituent thus described shows increase in its solubility to an organic liquid such as olive oil. Among these carbon chains, in particular, those having smaller number of carbon atoms are preferable because the smaller the number of carbon atoms they have, the more they can increase the water-solubility of the compound represented by the general formula (I).

It is preferable that a substituent, which binds to the oxo ring in the general formula (I) mentioned above, binds to α position or β position to a peroxy group in the oxo ring, that is, the sixth position or the seventh position of a 1,2,4,5-tetraoxane ring. The compound represented by the general formula (I) wherein a substituent binds to this position shows an increase in its solubility to a solvent even if there is a large number of members in the oxo ring.

As for the functional group represented by $R^0$ in the general formula (I) mentioned above, a hydroxyl group, a carboxyl group, an alkoxycarbonyl group, and a carbamoyl group, etc., are preferably exemplified. The alkoxycarbonyl group is not particularly limited, however, an alkoxycarbonyl group having an alkyl group having from 1 to 3 carbon atoms wherein $R^1$ is unsubstituted or optionally substituted in the general formula (II), is preferable. Examples of such alkoxycarbonyl group include a methoxycarbonyl group, an ethoxycarbonyl group, and an iso-propyloxycarbonyl group. Further, a lower alkyl group, such as a methyl group, an ethyl group, etc., is exemplified as a substituent, and a tert-butoxycarbonyl group, etc., are specifically exemplified as an alkoxycarbonyl group having such substituent.

Further, there is no particular limitation for an unsubstituted or optionally substituted carbamoyl group as a functional group represented by $R^0$ in the general formula (I) mentioned above, however, a carbamoyl group wherein $R^2$ and $R^3$ independently have any one of a hydrogen atom, an unsubstituted or optionally substituted methyl group or ethyl group in the general formula (III), is preferable. Specific examples of such carbamoyl group include; an unsubstituted carbamoyl group wherein $R^2$ and $R^3$ are hydrogen atoms, an N-methylcarbamoyl group, an N,N-dimethylcarbamoyl group, an N-ethylcarbamoyl group, an N,N-diethylcarbamoyl group, and an N,N-methylethylcarbamoyl group. As a substituent of a methyl group and an ethyl group, a hidroxyl group, etc., are exemplified, and as a carbamoyl group having a substituent, an N-hydroxymethyl carbamoyl group, an N,N-bis(hydroxymethyl)carbamoyl group, an N-hydroxyethyl carbamoyl group, an N,N-bis(hydroxyethyl)carbamoyl group, an N,N-hydroxymethyl hydroxyethyl carbamoyl group, etc., are specifically exemplified. In general, a compound represented by the general formula (I) having a carbamoyl group shows lower water-solubility in comparison to a compound represented by the general formula (I) having a hydroxyl group, however, a compound having an N,N-bis(hydroxyethyl)carbamoyl group shows remarkably improved water-solubility, and its solubility is also improved to acidic and neutral water, therefore, such compound is preferable.

In addition, as a functional group represented by $R^0$ in the general formula (I) mentioned above, a functional group which is a monoester group in a compound wherein alcohol, being represented by the general formula (I) in case where $R^0$ represents a hydroxyl group in the general formula (I), is esterified by dicarboxylic acid, and which is represented by the general formula (IV), is preferable. In the general formula (IV), Y is preferably an alkyl group, and the functional group is an ester group formed by combining alcohol, being represented by the general formula (I) in case where $R^0$ represents a hydroxyl group in the general formula (I), and aliphatic saturated dicarboxylic acid. Examples of aliphatic saturated dicarboxylic acid which forms such ester group include;

oxalic acid, malonic acid, succinic acid, glutaric acid, adipic acid, pimelic acid, suberic acid, azelaic acid, sebacic acid. In particular, acid having even number of carbon atoms such as succinic acid, adipic acid, suberic acid, that form ester groups having 2, 4, and 6 carbon atoms, respectively, Wherein Y is represented by any one of ethylene, tetraethylene, and hexamethylene groups in the general formula (IV), is preferable.

It is preferable that Y represents an ester group represented by the general formula (V) as a functional group represented by the general formula (IV) mentioned above. The functional group is an ester group formed by combining alcohol, being represented by the general formula (I) in case where $R^0$ represents a hydroxyl group in the general formula (I), and aliphatic unsaturated dicarboxylic acid. Examples of aliphatic unsaturated dicarboxylic acid which forms such ester group include maleic acid and fumaric acid.

Further, it is preferable that Y represents a phenylene group as a functional group represented by the general formula (IV) mentioned above. The functional group is an ester group formed by combining alcohol, being represented by the general formula (I) in case where $R^0$ represents a hydroxyl group in the general formula (I), and aromatic dicarboxylic acid. Examples of aromatic dicarboxylic acid which forms such ester group include phthalic acid, isophthalic acid, and terephthalic acid.

A pharmaceutically acceptable salt of the novel compound of the present invention is not particularly limited as long as it is a salt being pharmaceutically acceptable to the above-mentioned compound. Any salt can be used as long as generation of salt of the compound represented by the general formula (I) mentioned above leads to improved water-solubility of such compound. A pharmaceutically acceptable salt of any one of compounds wherein in the general formula (I), $R^0$ represents a carboxyl group or an alkoxycarbonyl group, or an ester group represented by the general formula (IV), is preferable. Examples of such salt include sodium salt, potassium salt, calcium salt, and ammonium salt, constructed by combing any one of compounds wherein in the general formula (I), $R^0$ represents a carboxyl group or an alkoxycarbonyl group, or an ester group represented by the general formula (IV), with bases of sodium ion, potassium ion, calcium ion, and ammonium ion, respectively. Such salt can increase water-solubility of the compound remarkably, in particular, sodium salt of a compound wherein in the general formula (I), $R^0$ represents an ester group represented by the general formula (IV), shows marked improvement of water-solubility, and therefore, is preferable.

Specific examples of the compound represented by the general formula (I) include;
9-hydroxymethyl-7,8,11,12-tetraoxaspiro[5.6]dodecane,
9-carboxy-7,8,11,12-tetraoxaspiro[5.6]dodecane,
9-methoxycarbonyl-7,8,11,12-tetraoxaspiro[5.6]dodecane,
9-carbamoyl-7,8,11,12-tetraoxaspiro[5.6]dodecane,
9-(N,N-bishydroxyethyl)carbamoyl-7,8,11,12-tetraoxaspiro[5.6]dodecane,
6-(7,8,11,12-tetraoxaspiro[5.6]dodecy-9-yl)hexane-1-ole,
5-(7,8,11,12-tetraoxaspiro[5.6]dodecy-9-yl)pentane-1-carboxylic acid,
5-(7,8,11,12-tetraoxaspiro[5.6]dodecy-9-yl)pentane-1-carboxylic acid methyl,
5-(7,8,11,12-tetraoxaspiro[5.6]dodecy-9-yl)pentane-1-carboxamide,
5-(7,8,11,12-tetraoxaspiro[5.6]dodecy-9-yl)pentane-1-(N,N-bishydroxyethyl)amide,
10-hydroxymethyl-7,8,12,13-tetraoxaspiro[5.7]tridecane,
10-carboxy-7,8,12,13-tetraoxaspiro[5.7]tridecane,
10-methoxycarbonyl-7,8,12,13-tetraoxaspiro[5.7]tridecane,
10-carbamoyl-7,8,12,13-tetraoxaspiro[5.7]tridecane,
10-(N,N-bishydroxyethyl)carbamoyl-7,8,12,13-tetraoxaspiro[5.7]tridecane,
6-(7,8,12,13-tetraoxaspiro[5.7]tridecy-10-yl)hexane-1-ole,
5-(7,8,12,13-tetraoxaspiro[5.7]tridecy-10-yl)pentane-1-carboxylic acid,
5-(7,8,12,13-tetraoxaspiro[5.7]tridecy-10-yl)pentane-1-carboxylic acid methyl,
5-(7,8,12,13-tetraoxaspiro[5.7]tridecy-10-yl)pentane-1-carboxamide, and
5-(7,8,12,13-tetraoxaspiro[5.7]tridecy-10-yl)pentane-1-(N,N-bishydroxyethyl)amide.

Specific examples of the compound represented by the general formula (I) further include;
11-hydroxymethyl-8,9,13,14-tetraoxaspiro[6.7]tetradecane,
11-carboxy-8,9,13,14-tetraoxaspiro[6.7]tetradecane,
11-methoxycarbonyl-8,9,13,14-tetraoxaspiro[6.7]tetradecane,
11-carbamoyl-8,9,13,14-tetraoxaspiro[6.7]tetradecane,
11-(N,N-bishydroxyethyl)carbamoyl-8,9,13,14-tetraoxaspiro[6.7]tetradecane,
6-(8,9,13,14-tetraoxaspiro[6.7]tetradecy-11-yl)hexane-1-ole,
5-(8,9,13,14-tetraoxaspiro[6.7]tetradecy-11-yl)pentane-1-carboxylic acid,
5-(8,9,13,14-tetraoxaspiro[6.7]tetradecy-11-yl)pentane-1-carboxylic acid methyl,
5-(8,9,13,14-tetraoxaspiro[6.7]tetradecy-11-yl)pentane-1-carboxamide,
5-(8,9,13,14-tetraoxaspiro[6.7]tetradecy-11-yl)pentane-1-(N,N-bishydroxyethyl)amide,
4-hydroxymethyl-1,2,6,7-tetraoxaspiro[7.9]heptadecane,
4-carboxy-1,2,6,7-tetraoxaspiro[7.9]heptadecane,
4-methoxycarbonyl-1,2,6,7-tetraoxaspiro[7.9]heptadecane,
4-carbamoyl-1,2,6,7-tetraoxaspiro[7.9]heptadecane,
4-(N,N-bishydroxyethyl)carbamoyl-1,2,6,7-tetraoxaspiro[7.9]heptadecane,
6-(1,2,6,7-tetraoxaspiro[7.9]heptadecy-4-yl)hexane-1-ole,
5-(1,2,6,7-tetraoxaspiro[7.9]heptadecy-4-yl)pentane-1-carboxylic acid,
5-(1,2,6,7-tetraoxaspiro[7.9]heptadecy-4-yl)pentane-1-carboxylic acid methyl,
5-(1,2,6,7-tetraoxaspiro[7.9]heptadecy-4-yl)pentane-1-carboxamide, and
5-(1,2,6,7-tetraoxaspiro[7.9]heptadecy-4-yl)pentane-1-(N,N-bishydroxyethyl)amide.

Specific examples of the compound represented by the general formula (I) further include;
4-hydroxymethyl-1,2,6,7-tetraoxaspiro[7.11]nonadecane,
4-carboxy-1,2,6,7-tetraoxaspiro[7.11]nonadecane,
4-methoxycarbonyl-1,2,6,7-tetraoxaspiro[7.11]nonadecane,
4-carbamoyl-1,2,6,7-tetraoxaspiro[7.11]nonadecane,
4-(N,N-bishydroxyethyl)carbamoyl-1,2,6,7-tetraoxaspiro[7.11]nonadecane,
6-(1,2,6,7-tetraoxaspiro[7.11]nonadecy-4-yl)hexane-1-ole,
5-(1,2,6,7-tetraoxaspiro[7.11]nonadecy-4-yl)pentane-1-carboxylic acid,
5-(1,2,6,7-tetraoxaspiro[7.11]nonadecy-4-yl)pentane-1-carboxylic acid methyl,
5-(1,2,6,7-tetraoxaspiro[7.11]nonadecy-4-yl)pentane-1-carboxamide,
5-(1,2,6,7-tetraoxaspiro[7.11]nonadecy-4-yl)pentane-1-(N,N-bishydroxyethyl)amide,
3-hydroxymethyl-1,2,7,8-tetraoxaspiro[8.11]eicosane,
3-carboxy-1,2,7,8-tetraoxaspiro[8.11]eicosane, 3-methoxycarbonyl-1,2,7,8-tetraoxaspiro[8.11]eicosane,
3-carbamoyl-1,2,7,8-tetraoxaspiro[8.11]eicosane,
3-(N,N-bishydroxyethyl)carbamoyl-1,2,7,8-tetraoxaspiro[8.11]eicosane,
6-(1,2,7,8-tetraoxaspiro[8.11]eicosi-3-yl)hexane-1-ole,
5-(1,2,7,8-tetraoxaspiro[8.11]eicosi-3-yl)pentane-1-carboxylic acid,
5-(1,2,7,8-tetraoxaspiro[8.11]eicosi-3-yl)pentane-1-carboxylic acid methyl,
5-(1,2,7,8-tetraoxaspiro[8.11]eicosi-3-yl)pentane-1-carboxamide, and
5-(1,2,7,8-tetraoxaspiro[8.11]eicosi-3-yl)pentane-1-(N,N-bishydroxyethyl)amide, and sodium salt, potassium salt, calcium salt, ammonium salt, etc., thereof.

Specific examples of ester of the compound wherein $R^0$ represents a hydroxyl group in the general formula (I) include;
10-(5'-carboxy-3'-oxo-2'-oxypentyl)-7,8,12,13-tetraoxaspiro[5.7]tridecane,
10-(10'-carboxy-8'-oxo-7'-oxydecyl)-7,8,12,13-tetraoxaspiro[5.7]tridecane,
10-(7'-carboxy-3'-oxo-2'-oxyheptyl)-7,8,12,13-tetraoxaspiro[5.7]tridecane,
10-(12'-carboxy-8'-oxo-7'-oxydodecyl)-7,8,12,13-tetraoxaspiro[5.7]tridecane,
10-(9'-carboxy-3'-oxo-2'-oxynotyl)-7,8,12,13-tetraoxaspiro[5.7]tridecane,
10-(14'-carboxy-8'-oxo-7'-oxytetradecyl)-7,8,12,13-tetraoxaspiro[5.7]tridecane,
10-(5'-carboxy-5'-en-3'-oxo-2'-oxypentyl)-7,8,12,13-tetraoxaspiro[5.7]tridecane,
10-(10'-carboxy-10'-en-8'-oxo-7'-oxydecyl)-7,8,12,13-tetraoxaspiro[5.7]tridecane,
10-(p-benzoylcarbonyl)-7,8,12,13-tetraoxaspiro[5.7]tridecane,
4-(5'-carboxy-3'-oxo-2'-oxypentyl)-1,2,6,7-tetraoxaspiro[7.11]nonadecane,
4-(10'-carboxy-8'-oxo-7'-oxydecyl)-1,2,6,7-tetraoxaspiro[7.11]nonadecane,
4-(7'-carboxy-3'-oxo-2'-oxyheptyl)-1,2,6,7-tetraoxaspiro[7.11]nonadecane,
4-(12'-carboxy-8'-oxo-7'-oxydodecyl)-1,2,6,7-tetraoxaspiro[7.11]nonadecane,
4-(9'-carboxy-3'-oxo-2'-oxyheptyl)-1,2,6,7-tetraoxaspiro[7.11]nonadecane,
4-(14'-carboxy-8'-oxo-7'-oxytetradecyl)-1,2,6,7-tetraoxaspiro[7.11]nonadecane,
4-(5'-carboxy-5'-en-3'-oxo-4'-oxypentyl)-1,2,6,7-tetraoxaspiro[7.11]nonadecane,
4-(10'-carboxy-10'-en-8'-oxo-7'-oxydecyl)-1,2,6,7-tetraoxaspiro[7.11]nonadecane, and
4-(p-benzoylcarbonyl)-1,2,6,7-tetraoxaspiro[7.11]nonadecane, and sodium salt, potassium salt, calcium salt, ammonium salt, etc., thereof.

There is no particular limitation for a method for producing the compound represented by the general formula (I) thus described. For instance, it is possible to apply a producing method wherein an oxo ring is generated by combining a dihalide (viii) generated by the following steps, with the use of diester of dicarboxylic acid represented by the formula (VI), etc., as a start material (i), with a bishydroperoxide compound (x) generated with the use of alicyclic hydrocarbon (ix) represented by the formula (VII) as a start material.

(Chemical formula 11)

(VI)

(i) → NaOEt, (ii) RBr → (iii) R = THPO(CH$_2$)$_6$ → (iv) LAH → (v) → Pyridine, (vi) MsCl → (vii) → NaZ → (viii)

(Chemical formula 12)

(VII)

(ix) → (x)

Diester (i), and a halide (ii) of alkyl group R having a substituent such as tetrahydropyran-2-yloxy group (THPO), a derivative of pyran, at its terminus (THPO(CH$_2$)$_6$), are made to react in the presence of such as ethanol solution of sodium ethoxide obtained by adding sodium to ethanol, and a substituent R is introduced into diester of dicarboxylic acid (iii) (step <1>). The halide (ii) used in step <1> can be synthesized by the method previously described [G. Berube, P. Wheeler, C. H. J. Ford, M. Gallant, and Z. Tsaltas, Can. J. Chem., 71, 1327 (1993)], and the halide may be fluoride, chloride, bromide, iodide, etc., however, bromide is preferable. The reaction of step <1> can be conducted within a temperature range of 20 to 80° C., preferably around 50° C., using 1 to 5, preferably 1 to 2 equimolar amounts of the halide (ii) to the compound (i), and preferable reaction time is 2 to 5 hours. The obtained compound (iii) can be easily isolated and purified from the reaction mixture by ordinary methods of separation such as column chromatography, recrystallization, and the like.

In the presence of lithium aluminum hydride (LAH) (iv), diester of dicarboxylic acid into which the substituent R is introduced is transformed to be diol (v) (step <2>). It is preferable that step <2> is conducted in the presence of a solvent, such as ether, and the reaction can be conducted within a temperature range of 0 to 50° C., preferably around 0° C. After the reaction, aluminum salt, a byproduct of the reaction, can be removed by suction filtration using celite or the like. In the reaction, 1 to 5, preferably 2 equimolar amounts of lithium aluminum hydride (iv) is used to the compound (iii) into which the substituent R is introduced, and preferable reaction time is 1 to 5 hours. The obtained diol (v) can be easily isolated and purified from the reaction mixture by ordinary methods, for example, by drying over anhydrous magnesium sulfate, etc., refluxing a solvent under reduced pressure, and conducting column chromatography and the like.

In the presence of pyridine, the obtained diol is made to react with methanesulfonyl chloride (vi), and transformed to be dimesylate (vii) (step <3>). The reaction can be conducted within a temperature range of 0 to 40° C., preferably around 0° C. In the reaction, 2 to 10, preferably 2 to 8 equimolar amounts of methanesulfonyl chloride (vi) is used to diol (v), and preferable reaction time is 1 to 4 hours. The obtained dimesylate (vii) can be easily isolated and purified from the reaction mixture by ordinary methods, for example, by drying over anhydrous magnesium sulfate, etc., and conducting column chromatography, recrystallization, and the like.

Further, dimesylate obtained in step <3> is made to react with alkali metal halide, and transformed to be dihalide (viii) (step <4>). The reaction of step <4> is preferably conducted in the presence of a solvent, such as dimethylformamide, with the use of sodium iodide as alkali metal halide. The reaction can be conducted by the following steps; heating alkali metal halide to a temperature range of 50 to 100° C., preferably around 70° C. in order to dissolve alkali metal halide in a solvent such as dimethylformamide, lowering the temperature to a temperature range of 30 to 60° C., preferably around 50° C., and adding dimesylate obtained in step <3>. In the reaction, 2 to 10, preferably 2 to 4 equimolar amounts of alkali metal halide is used to dimesylate (vii), and preferable reaction time is 2 to 10 hours. The obtained dihalide (viii) can be easily isolated and purified from the reaction mixture by ordinary methods, for example, by drying over anhydrous magnesium sulfate, etc., and conducting column chromatography, recrystallization, and the like.

On the other hand, bishydroperoxide compound (x) represented by the formula (VII) can be synthesized by the method according to the description in J. Org. Chem., 62, 4949 (1997). In other words, with the use of alicyclic hydrocarbon having a methoxymethylene group as a start material (ix), bishydroperoxide compound (x) can be obtained by reacting a compound (ix) with ozone in an appropriate solvent in the presence of hydrogen peroxide. There is no particular limitation for a solvent as long as it is not involved in the reaction, and ether, tetrahydrofran, acetonitrile, etc., are exemplified as such solvent. Among them, ether is preferable. In the reaction, 30 to 100 wt % of hydrogen peroxide can be used, and 1 to 10, preferably 1 to 3 equimolar amounts of hydrogen peroxide, and 0.5 to 5, preferably 1 to 2 equimolar amounts of ozone can be used to the compound (ix). It is preferable that reaction temperature is −70 to 20° C., and reaction time can be 5 to 30 minutes. The obtained bishydroperoxide compound (x) can be easily isolated and purified from the reaction mixture by ordinary methods of separation such as column chromatography, recrystallization, and the like, however, it can be used to the reaction with dimesylate obtained by the above-mentioned method irrespective of isolation.

The reaction of bishydroperoxide compound (x) and dihalide (viii), both obtained by the method mentioned above, can be conducted according to the method previously reported [K. J. McCullough, Y. Nonami, A. Masuyama, M. Nojima, H. -S. im, and Y. Wataya, Tetrahedron Lett., 40, 9151-9155 (1999)]. In other words, the reaction can be conducted by adding a solvent containing bishydroperoxide compound (x) to a solvent containing silver oxide represented by the formula (VIII), within a temperature range of 0 to 40° C., preferably at room temperature. In the reaction, ethyl acetate, etc., can be used as a solvent, and 1 to 2, preferably 1.5 equimolar amounts of dihalide is used to bishydroperoxide compound (x), and reaction time can be 2 to 15 hours. Silver halide, a byproduct of the reaction, is removed by suction filtration using celite, and the solvent is refluxed under reduced pressure. Tetraoxo ring compound (xi) having a substituent R can be easily isolated and purified from the reaction mixture by ordinary methods, for example, column chromatography, recrystallization, and the like.

(Chemical formula 13)

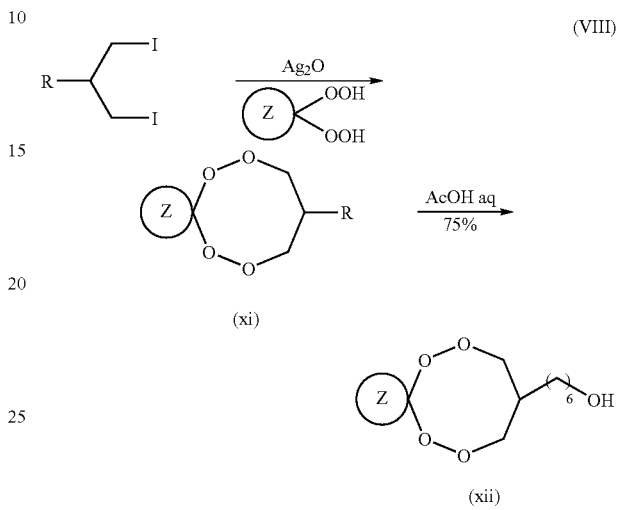

For the introduction of a hydroxyl group into the substituent R in the tetraoxo ring compound (xi) obtained by the method mentioned above, in case where the substituent R is an alkyl group having a tetrahydropyran-2-yloxy group, a derivative of pyran, etc., at its terminus, a terminal group can be substituted with a hydroxyl group at room temperature in the presence of aqueous acetic acid solution. In the reaction, 50 to 500 equimolar amounts of acetic acid can be used to tetraoxo ring compound (xi), and reaction time can be 10 to 30 hours. After the reaction, silver halide, a byproduct of the reaction, is removed by suction filtration using celite, and the solvent is refluxed under reduced pressure, thus hydroxyalkyltetraoxo ring compound (xii) wherein a hydroxyl group is introduced into a terminus of the substituent R can be obtained. The hydroxyalkyltetraoxo ring compound (xii) can be easily isolated and purified from the reaction mixture by ordinary methods, for example, by drying over anhydrous magnesium sulfate, etc., and conducting column chromatography, recrystallization and the like.

Further, ester represented by the general formula (IV) can be produced by esterifying the hydroxyalkyltetraoxo ring compound (xii) obtained by the above-mentioned method with dicarboxylic acid such as succinc acid. The reaction of hydroxyalkyltetraoxo ring compound (xii) and dicarboxylic acid can be conducted according to known methods in the presence of an acid catalyst such as sulfuric acid, hydrogen chloride, etc., and a base catalyst such as pyridine, etc. The reaction can be conducted at room temperature, and 1 to 2, preferably 1.5 equimolar amounts of dicarboxylic acid is used to hydroxyalkyltetraoxo ring compound (xii), and reaction time can be 10 to 15 hours.

In addition, an example of a method for producing a pharmaceutically acceptable salt of a compound represented by the general formula (I) includes a method comprising the steps of; adding hydroxyalkyltetraoxo ring compound (xii) obtained by the above-mentioned method, etc., to an aqueous solution containing metal ion etc. that constitutes salt together with a compound represented by the general formula (I), such as sodium hydrogen carbonate solution, and stirring the resultant solution. The method can be conducted at room temperature, or, if necessary, the solution may be appropriately heated.

In case a compound represented by the general formula (I) or salt thereof is used to prevent, suppress, and treat an infection caused by malaria parasites, one or more kinds of the above-mentioned compounds or salt thereof can be mixed and used appropriately. As an administration route, not only oral route, but also any one of subcutaneous injection, intravenous injection, topical administration, etc. can be selected because of improved water-solubility. Examples of drugs usually include those for oral administration such as powders, tablets, subtle granules, pills, capsules, granules or the like, and those for parenteral administration such as eye-drops, injectable solutions, suppositories or the like, all formulated by using pharmaceutically acceptable carriers, excipients and other additives. Examples of pharmaceutically acceptable carriers, excipients and other additives include glucose, lactose, gelatin, mannitol, starch paste, magnesium trisilicate, corn starch, keratin, coloidal silica, and it may further contain adjuvants such as a stabilizer, an expander, a colorant and an aromatic substance. Each of these drugs can be produced by methods known and commonly used by a person skilled in the art.

The present invention is explained more specifically below with reference to examples, but the technical scope of the present invention is not limited to these examples.

EXAMPLE 1

Synthesis of 2-[6-(tetrahydropyran-2-yloxy)hexyl]diethylester maleate (iii)

75 ml of ethanol was put into a 300 ml, four-necked recovery flask equipped with a reflux condenser and a dropping funnel, and 805 mg of thin slices of sodium (35.00 mmol) was added little by little. This ethanol solution of sodium ethoxide was kept at about 50° C., 5600 mg of diethylmalonate (35.00 mmol) was added dropwise with a dropping funnel for about 1 hour, and then 927 mg of 2-(6-bromohexyloxy)tetrahydropyran (35.00 mmol), separately synthesized by the method previously described [G. Berube, P. Wheeler, C. H. J. Ford, M. Gallant, and Z. Tsaltas, Can. J. Chem., 71, 1327 (1993)], was added dropwise for 1 hour in a similar manner, then the resultant solution was refluxed and stirred for 2 hours. After the reaction, a solvent was refluxed under reduced pressure at or below 40° C. Residues were put into water and subjected to ether extraction twice, dried over anhydrous magnesium sulfate, then the solvent was refluxed under reduced pressure at or below 40° C. By silica gel column chromatography of residues, 9006 mg of diester (iii) (yield 75%) was obtained as a fraction developed by hexan-ether, 85:15.

An oil; $^1$H NMR $\delta$ 1.27 (t, J=7.3 Hz, 6 H), 1.3-2.0 (m, 16 H), 3.31 (t, J=6.6 Hz, 1 H), 3.38 (m, 1 H), 3.50 (m, 1 H), 3.74 (m, 1 H), 3.87 (m, 1 H), 4.19 (q, J=7.3 Hz, 4 H), 4.58 (t, J=3.5 Hz, 1 H), $^{13}$C NMR $\delta$ 14.02, 19.63, 25.41, 25.90, 27.21, 28.61, 29.00, 29.54, 30.69, 51.95, 61.19, 62.28, 67.44, 98.78, 169.51.

EXAMPLE 2

Synthesis of 2-[6-(tetrahydropyran-2-yloxy)hexyl]propane-1,3-diol (v)

A suspension of 2280 mg of lithium aluminum hydride (hereinafter referred to as LAH) (60.00 mmol) and 100 ml of ether was prepared in a 300 ml, four-necked recovery flask equipped with a reflux condenser and a dropping funnel, and 10.32 g of diester (iii) (30 mmol) obtained in Example 1 was added dropwise slowly at 0° C., then the resultant suspension was stirred for 1 hour at room temperature. After the reaction, aqueous sodium hydrate solution was added, and the resultant aluminum salt was removed by suction filtration using celite. The filtered solution was subjected to ether extraction twice, dried over anhydrous magnesium sulfate, then a solvent was refluxed under reduced pressure at or below 40° C. By silica gel column chromatography of residues, 5123 mg of diol (v) (yield 66%) was obtained as a fraction developed by hexan-ether, 0:100.

An oil; $^1$H NMR $\delta$ 1.2-1.9 (m, 17 H), 2.44 (br s, 2 H), 3.35 (d, J=6.6 Hz, 2 H), 3.38 (m, 1 H), 3.41 (d, J=6.6 Hz, 2 H), 3.50 (m, 1 H), 3.74 (m, 1 H), 3.87 (m, 1H), 4.57 (t, J=3.5 Hz, 1 H), $^{13}$C NMR $\delta$ 19.54, 25.29, 25.93, 26.96, 27.53, 29.47, 29.53, 30.59, 41.76, 62.32, 65.70, 67.53, 98.80.

EXAMPLE 3

Synthesis of 2-methanesulfonyloxymethyl-8-(tetrahydropyran-2-yloxy)octyl ester (vii)

3640 mg of diol (v) (14.00 mmol) obtained in Example 2 and 3220 mg of methanesulfonyl chloride (28.00 mmol) were added to a 100 ml recovery flask, and 4424 mg of pyridine (56.00 mmol) was added dropwise slowly at 0° C., then the resultant solution was stirred for 1 hour at room temperature. After the reaction, the solution was put into 10% of hydrochloric acid, subjected to ether extraction twice, washed with saturated saline, and dried over anhydrous magnesium sulfate, then a solvent was refluxed under reduced pressure at or below 40° C. By silica gel column chromatography of residues, 4333 mg of dimesylate (vii) (yield 74%) was obtained as a fraction developed by hexan-ethyl acetate, 65:35.

An oil; $^1$H NMR $\delta$ 1.2-1.9 (m, 17 H), 3.05 (s, 6 H), 3.38 (m, 1 H), 3.50 (m, 1 H), 3.74 (m, 1 H), 3.87 (m, 1 H), 4.21 (d, J=6.6 Hz, 2 H), 4.27 (d, J=6.6 Hz, 2 H), 4.57 (t, J=3.5 Hz, 1 H), $^{13}$C NMR $\delta$ 19.70, 25.41, 25.99, 26.47, 26.88, 29.29, 29.56, 30.73, 37.25, 38.12, 62.41, 67.44, 68.16, 98.89.

EXAMPLE 4

Synthesis of 2-(8-iode-7-iodemethyl octyloxy)tetrahydropyran (viii)

100 ml of dimethylformamide (DMF) and 4500 mg of sodium iodide (30.00 mmol) was added to a 100 ml recovery flask, and the resultant solution was heated to 70° C. to dissolve sodium iodide completely, then cooled to 50° C. 4160 mg of dimesylate (vii) (10.00 mmol) obtained in Example 3 was added, and the resultant solution was stirred for 2 hours at room temperature. After the reaction, the solution was added with water and stirred for 5 minutes, subjected to ether extraction 3 times, washed with saturated saline, and dried over anhydrous magnesium sulfate, then a solvent was refluxed under reduced pressure at or below 40° C. By silica gel column chromatography, 2810 mg of diiodide (viii) (yield 59%) was obtained as a fraction developed by hexan-ether, 95:5.

An oil; $^1$H NMR δ 1.2-1.9 (m, 17 H), 3.19 (d, J=6.0 Hz, 2 H), 3.23 (d, J=6.0 Hz, 2 H), 3.38 (m, 1 H), 3.50 (m, 1 H), 3.74 (m, 1 H), 3.87 (m, 1 H), 4.57 (t, J=3.5 Hz, 1 H), $^{13}$C NMR δ 14.25, 19.59, 25.38, 25.95, 26.70, 29.15, 29.51, 30.64, 34.13, 40.34, 63.25, 67.37, 98.71.

EXAMPLE 5

Synthesis of (cyclododecylidene)bishydroperoxide (x)

630 mg of methoxymethylene cyclododecane (3.00 mmol), a known compound, was dissolved into 25 ml of ether solution containing 2.5 mol of hydrogen peroxide prepared by the method of Saito et al. (Saito, I.; Nagata, R.; Yuba, K.; Matuura, T. Tetrahedron Lett. 1983, 24, 1737), and ozonization was conducted at −70° C. The ozonization was conducted as follows: with the use of an ordinary ozonization apparatus (Nippon Ozone Model ON-1-2; Nihon Ozone Co., Ltd.), oxygen was blown for 15 minutes at a flow velocity of 50 l/hr to generate ozone of the same quantity as methoxymethylene cyclododecane used. After the reaction, 70 ml of ether was added, and an organic layer was washed with sodium bicarbonate water, and subsequently with saturated saline, and then dried over anhydrous magnesium sulfate. By silica gel column chromatography, 232 mg of bishydroperoxide (x) (yield 33%) was obtained as a fraction developed by ether-hexan, 2:8.

mp. 140-141° C., $^1$H NMR (CDCl3) δ 1.2-1.8 (m, 22H), 8.13 (brs, 2H), $^{13}$C NMR (CDCl3) δ 19.28, 21.86, 22.15, 6.02, 26.19, 26.29, 112.64.

EXAMPLE 6

Synthesis of (4-tert-butylcyclohexylidene)bishydroperoxide (x)

546 mg of 4-tert-butyl-2-methoxymethylene cyclohexane (3.00 mmol) was dissolved into 25 ml of ether solution containing hydrogen peroxide prepared in a same manner as that of Example 5, and ozonization was conducted at −70° C. After the reaction, the same treatment as that of Example 5 was conducted. Subsequently, by silica gel column chromatography, 285 mg of bishydroperoxide (x) (yield 47%) was obtained as a fraction developed by ether-hexan, 2:8.

mp. 83-84° C. (ether-hexane), $^1$HNMR (CDCl3) δ 0.87 (s, 9H), 1.1-1.8 (m, 9H), 9.27 (s, 2H), $^{13}$C NMR (CDCl3) δ 23.32, 27.58, 29.70, 32.31, 47.39, 110.00. Anal. Clacd. for $C_{10}H_{20}O_4$: C, 58.80, H, 9.87. Found: C, 58.87, H, 9.80.

EXAMPLE 7

Synthesis of (2-adamantylidene)bishydroperoxide (x)

712 mg of 2-methoxymethylene adamantane (4.00 mmol) was dissolved into 25 ml of ether solution containing hydrogen peroxide prepared in a same manner as that of Example 5, and ozonization was conducted at −70° C. After the reaction, the same treatment as that of Example 5 was conducted. Subsequently, by silica gel column chromatography, 335 mg of bishydroperoxide (x) (yield 42%) was obtained as a fraction developed by ether-hexan, 2:8.

mp. 144-145° C. (ether-hexane), $^1$H NMR (CDCl3) δ 1.7-2.1 (m, 14H), 8.82 (s, 22H), $^{13}$C NMR (CDCl3) δ 26.94, 31.14, 33.68, 33.98, 112.88, 33.98, 37.25, 73.94, 109.95.

EXAMPLE 8

Synthesis of 4-[6-(tetrahydropyran-2-yloxy)]-1,2,6,7-tetraoxaspiro[7.11]nonadecane (xi)

Synthesis was conducted with reference to the method previously reported [K. J. McCullough, Y. Nonami, A. Masuyama, M. Nojima, H.-S. Kim, and Y. Wataya, Tetrahedron Lett., 40, 9151-9155 (1999)]. In other words, under nitrogen atmosphere, 5 ml of ethyl acetate solution containing 232 mg of cyclododecylidene bishydroperoxide (1.00 mmol) separately synthesized by the method previously described [T. Ledaal and T. solbjoer, Acta Chem. Scand., 21, 1658 (1967)] was added dropwise, at room temperature while stirring, to 5 ml of ethyl acetate suspension containing 8464 mg of silver oxide (2.00 mmol) in a 50 ml recovery flask. Then, 5 ml of ethyl acetate solution containing 720 mg of diiodide (viii) (1.50 mmol) obtained in Example 4 was added dropwise, and the resultant solution was stirred at room temperature for 15 hours. After the reaction, silver iodide, a byproduct, was removed by suction filtration using celite, and a solvent was refluxed under reduced pressure at or below 40° C. By silica gel column chromatography of residues, 70 mg of cyclododecanone (yield 38%), a degradation product, was obtained as a fraction developed by hexan-ether, 95:5, and then, 181 mg of tetroxocane (xi) (yield 40%) was obtained as a fraction developed by hexan-ether, 92:8.

mp. 42-44° C. (hexane), $^1$H NMR δ 1.2-1.8 (m, 38H), 2.4-2.5 (m, 1H), 3.38 (m, 1H), 3.50 (m, 1H), 3.6-3.7 (m, 2H), 3.83 (m, 1H), 4.0-4.2 (m, 2H), 4.35 (m, 1H), 4.57 (t, J=3.5 Hz, 1H), $^{13}$C NMR δ 19.12, 19.39, 19.68, 21.85, 22.14, 25.45, 25.86, 26.00, 26.06, 26.18, 26.40, 27.05, 29.62, 30.73, 40.00, 62.37, 67.51, 79.17, 98.85, 112.09. Anal. Calcd. for $C_{26}H_{48}O_6$: C, 68.38, H, 10.60. Found: C, 68.10, H, 10.47.

EXAMPLE 9

Synthesis of 6-(1,2,6,7-tetraoxaspiro[7.11]nonadecy-4-yl)hexane-1-ole (xii)

228 mg of tetroxocane (xi) (0.50 mmol) obtained in Example 8, 4 ml of acetic acid, 2 ml of THF, and 1 ml of water were added to a 50 ml recovery flask, and the resultant solution was stirred for 15 hours at room temperature. After the reaction, the solution was put into aqueous sodium carbonate solution and subjected to ether extraction twice, washed with saturated saline, and then dried over anhydrous magnesium sulfate, a solvent was refluxed under reduced pressure at or below 40° C. By silica gel column chromatography of residues, 40 mg of tetroxocane (20% of the added amount), an unreacted material, was obtained as a fraction developed by hexan-ether, 90:10, and then, 140 mg of alcohol (xii) (yield 75%) was obtained as a fraction developed by hexan-ether, 68:32.

mp. 52-54° C. (hexane-ether), $^1$HNMR δ 1.2-1.8 (m, 32H), 2.16 (m, 1H), 2.45 (br s, 1H), 3.64 (t, J=6.6Hz, 2H), 3.70 (m, 2H), 4.0-4.2 (m, 1H), 4.3-4.4 (m, 1H), $^{13}$C NMR δ 19.23, 19.98, 21.73, 22.01, 25.45, 25.72, 25.86, 26.04, 26.96, 28.90, 32.40, 39.86, 62.46, 78.98, 111.95. Anal. Calcd. for $C_{21}H_{40}O_5$: C, 67.70, H, 10.82. Found: C, 67.44, H, 10.59.

EXAMPLE 10

Solubility of Cyclic Peroxide Compounds and Derivatives Thereof

As to 6-(1,2,6,7-tetraoxaspiro[7.11]nonadecy-4-yl)hexane-1-ole (N251), 5-(1,2,6,7-tetraoxaspiro[7.11]nonadecy-4-yl)pentane-1-carboxylic acid (N251-1), succinic acid mono-[6-(1,2,6,7-tetraoxaspiro[7.11]nonadecy-4-yl)hexyl] ester (N251-2), all obtained in Example 9, and 1,2,6,7-tetraoxaspiro[7.11]nonadecane (N89), artemisinin, artesunate (trade name: Guilin No. 2, Pharmaceutical Factory, Guangxi, China) as comparative examples, solubility to 5% of sodium bicarbonate water and dimethylsulfoxide (DMSO) was measured. The results are shown in Table 1.

TABLE 1

|  |  | 5% of sodium bicarbonate water | DMSO |
|---|---|---|---|
| Examples | N251 |  | insoluble |
|  | N251-1 | 50 mg/ml |  |
|  | N251-2 | 100 mg/ml |  |
| Comparable examples | N-89 |  | insoluble |
|  | artemisinin |  | insoluble |
|  | artesunate | 100 mg/ml |  |

EXAMPLE 11

Culture Test of *Plasmodium falciparum*

As *Plasmodium falciparum*, *P. falciparum* FCR-3 strain (ATCC30932) was used, and chloroquine-resistant malaria parasite of *P. falciparum* K-1 strain was used in order to examine the effect of the compound of the present invention on a strain being resistant to chloroquine, a commercially available antimalarial agent. A filter-sterilized RPMI1640 medium (pH 7.4) was added with human serum such that the serum made up 10% of the medium, and used in the experiment. *P. falciparum* were cultured in $O_2$ at a concentration of 5%, $CO_2$ at a concentration of 5% and $N_2$ at a concentration of 90%, at a temperature of 36.5° C. Hematocrit value (ratio of volume of erythrocytes in erythrocyte suspension) was adjusted to be 5%, and initial infection rate of *P. falciparum* at the beginning of culture was adjusted to be 0.1%. A 24-well plate was used for culture and a medium was replaced everyday, and cultures were transferred at infection rate of 4%. A thin-layer smear was constructed and subjected to Giemsa staining or Diff-Qick staining, and followed by measurement under a microscope (oil immersion, 1000×), and then infection rate of *P. falciparum* was calculated according to the following formula.

Infection rate of *P. falciparum* (%)={(number of infected erythrocytes)/(total number of erythrocytes)}×100

EXAMPLE 12

Growth Inhibition Screening Test of *P. falciparum*

Cultured erythrocytes infected with *P. falciparum* were gathered by centrifugation and washed with a medium containing serum, then noninfected erythrocytes were added, and initial infection rate was adjusted to be 0.3%. Hematocrit value in this case was 3%. 6-(1,2,6,7-tetraoxaspiro[7.11] nonadecy-4-yl)hexane-1-ole (N251) obtained in Example 9, and 1,2,6,7-tetraoxaspiro[7.11]nonadecane (N89), chloroquine, artemisinin, artesunate, as comparable examples, were used as samples in the experiment. These samples were dissolved into sterilized water, dimethylformamide (DMF) or dimethylsulfoxide (DMSO), and sample solutions at prescribed concentration were prepared. 5 to 10 μl each of the sample solutions was added to a 24-well culture plate. For each sample, 2 to 3 experiments were conducted. In addition, for control, sterilized water, DMF or DMSO was added by 10 μl/well. Next, the above-mentioned culture liquid for *P. falciparum* prepared to be of prescribed concentration or chloroquine-resistant *P. falciparum* was added, by 990 to 995 μl each, and uniformly suspended in media by pipetting gently. The culture plate was put into a $CO_2$—$O_2$—$N_2$ (5%, 5%, 90%) incubator and culture was conducted for 72 hours, then a thin-layer smear was constructed for each well, Giemsa staining or Diff-Qick staining was conducted, followed by measurement under a microscope (oil immersion, 1000×), and then infection rates of *P. falciparum* in a group supplemented with a reagent and in controls were calculated. The growth rate was calculated according to the following formula based on the infection rate of *P. falciparum* as calculated above.

Growth rate (%)={([b]−[a])/([c]−[a])}×100 a: initial infection rate
b: infection rate when sample solution added
c: infection rate of a control Based on the calculated growth rate, $EC_{50}$, a concentration where growth of 50% of *P. falciparum* is inhibited, was calculated. $EC_{50}$ is a value expressed by molar concentration: when growth rate of control wherein sample solution is not added to a medium of *P. falciparum* is defined as 100%, $EC_{50}$ indicates a concentration of a sample wherein infection rate of *P. falciparum* in control is inhibited by 50% due to the addition of sample solution. The results are shown in Table 2.

EXAMPLE 13

Growth Inhibition Test of Mouse FM3A Cells

An F28-7 strain, a wild-type strain of mouse breast cancer-derived FM3A cells, was used. Immobilized fetal bovine serum was added to an ES medium such that the serum made up 2% of the medium, and culture was conducted in $CO_2$ at a concentration of 5%, and at 37° C. Doubling time of FM3A cells under this condition was about 12 hours. Cells which had been precultured and entered to logarithmic growth phase were diluted to be $5 \times 10^4$ cells/ml in the medium. A sample prepared at the time of the measurement of antimalarial activity of *P. falciparum* was used. 5 to 10 μl of the sample solution prepared in Example 11 was added to each well of a 24-well culture plate. For each test sample, 2 to 3 experiments were conducted, and wells added with 10 μl each of sterilized water, DMF and DMSO were tested at the same time as controls. Next, a prepared suspension of cultured cells was added, by 990 to 995 μl each, and when medium and the like were added, the final concentration of test samples became $1 \times 10^{-4}$ to $1 \times 10^{-6}$ M. By pipetting gently, these substances were uniformly suspended in media. After cultured for 48 hours, the number of cells in each well was counted by a cell controller (CC-108; To a Medical Electrics).

Based on the counted number of cells, growth rate was calculated by the following formula.

Growth rate (%)={([C]−[A])/([B]−[A])}×100

A: the number of cells at the beginning
B: the number of cells in a control after 48 hours C: the number of cells 48 hours after sample addition Based on the calculated growth rate, $IC_{50}$, cell growth inhibitory concentration, was calculated, and cytotoxicity of samples was evaluated as cell growth inhibitory activity. $IC_{50}$ is a value expressed by molar concentration: when growth rate of a medium of FM3A cells to which a control, which has not been added with sample solution, is added, is defined as 100%, $IC_{50}$, cell growth inhibitory concentration, indicates a concentration of a sample wherein growth rate of control is inhibited by 50% due to the addition of sample solution. The results are shown in Table 2.

EXAMPLE 14

Assessment of Drug Efficacy

Evaluation of antimalarial activity of samples was conducted on the basis of chemotherapeutic coefficient used as an index of selective toxicity against *P. falciparum*. Chemotherapeutic coefficient was calculated by the following formula as a ratio of $EC_{50}$ value of each sample used for *P. falciparum* to $IC_{50}$ value of each sample used for mouse FM3A cells, and drug efficacy was assessed based on the calculated values. The results are shown in Table 2.

Chemotherapeutic coefficient=($IC_{50}$ value of the sample for mouse FM2A cells)÷($EC_{50}$ value of the sample for *P. falciparum*)

TABLE 2

| Samples | EC$_{50}$ (M) | | IC$_{50}$ (M) | |
|---|---|---|---|---|
| | *P. falciparum* FCR-3 | Chloroquine-resistant *P. falciparum* K1 | Cancer cells of mice FM3A | IC$_{50}$/EC$_{50}$ Chemotherapeutic coefficient |
| N251 | 2.3 × 10$^{-8}$ | 2.0 × 10$^{-8}$ | 8 × 10$^{-6}$ | 348 |
| N89 | 2.5 × 10$^{-8}$ | 2.6 × 10$^{-8}$ | 8.2 × 10$^{-6}$ | 328 |
| Chloroquine | 1.8 × 10$^{-8}$ | 1.3 × 10$^{-7}$ | 3.2 × 10$^{-5}$ | 1780 |
| Artemisinin | 1 × 10$^{-8}$ | 1.3 × 10$^{-8}$ | 1 × 10$^{-5}$ | 1000 |

Based on the above-mentioned results, it is revealed that the compound of the present invention has better selective toxicity than conventional compounds, growth inhibition activity against *P. falciparum*, and excellent drug efficacy. Moreover, it is revealed that the compound of the present invention has excellent antimalarial activity against chloroquine-resistant *P. falciparum*, as well.

EXAMPLE 15

Parasite Suppression Test Using Mice Infected with Murine Malaria Parasite

This experiment was conducted according to 4-day suppressive test described in Peters, W. and Richards, W. H. G. Antimalarial drugs I, in: W. Peters, W. H. G. Richards (Eds.), Springer-Verlag, Berlin, 1984, pp. 229-230. The murine malaria parasites used (*P. berghei* NK65 strain) were high virulent parasite strain, and all mice infected with this murine malaria parasite will die within 10 days after the infection. The experiment was started when in-blood infection rate of mice infected with subcultured murine malaria parasite reached 10%. Mice were anesthetized with ether, and blood was collected from hearts. 200 µl of parasite suspension, prepared to be 5×10$^6$ parasites per 1 ml of phosphate buffered saline, was intraperitoneally (i. p.) injected in to uninfected mice. After 2 hours from the parasite infection, the compound suspended in olive oil was orally or intraperitoneally administered. The administration was conducted once a day for 4 days in a row, and on the 4$^{th}$ day of the experiment, blood was collected from tails of mice. A thin-layer smear was constructed with collected blood and subjected to Giemsa staining, and infection rate in erythrocytes was examined under a microscope in a same manner as that of Example 11. By examining the ratio of infection rate in a drug-administered group to that in a control group administered with a solvent only, $ED_{50}$, a concentration where 50% of parasites are suppressed, and $ED_{90}$, a concentration where 90% of parasites are suppressed, were calculated. The results are shown in Table 3.

TABLE 3

| | ED$_{50}$ (mg/kg) | ED$_{90}$ (mg/kg) | |
|---|---|---|---|
| N251 | <10 [<7 on N89 basis] | 18 [13 on N89 basis] | All cured with 50 mg/kg |
| N89 | 12 | 20 | All cured with 50 mg/kg |
| Chloroquine | 1.8 | 3 | Not cured |
| Artemisinin | 6 | 10.3 | Not cured |

It is revealed that the compound of the present invention is more excellent than the compound N89 with regard to the exhibition of mg/kg concentration and molar concentration of the parasite suppressive concentration, and that it has excellent growth inhibitory activity against *P. falciparum* in vivo.

INDUSTRIAL APPLICABILITY

The novel compound of the present invention can be applied as an antimalarial agent, and the antimalarial agent of the present invention has excellent antimalarial activity with little side effects. In particular, it has remarkable antimalarial activity against drug-resistant malaria parasites, and is capable of increasing solubitiy not only to organic solvent including olive oil, but also to water, and therefore it can be used not only as oral drugs but also as injectable solutions, and can expand the scope of application significantly.

The invention claimed is:

1. A compound represented by the general formula (I);

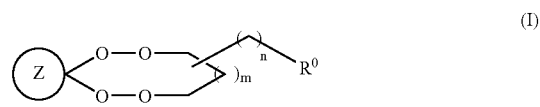

(I)

wherein Z represents cyclododecyl or cyclohexyl, optionally substituted with an alkyl, or Z represents adamantyl, R$^0$ represents a hydroxy group, m is 1, and n represents any one of integers of from 1 to 10, or a pharmaceutically acceptable salt thereof.

2. A pharmaceutically acceptable salt of the compound according to claim 1.

* * * * *